US005739245A

United States Patent [19]
Lübbers et al.

[11] Patent Number: 5,739,245
[45] Date of Patent: Apr. 14, 1998

[54] PLASTICS WITH A CONTENT OF SILANE, ETHER, URETHANE AND UREA GROUPS AND THEIR USE AS DENTAL COMPOSITION

[75] Inventors: Dierk Lübbers; Wolfgang Mühlbauer, both of Hamburg, Germany

[73] Assignee: Ernst Mühlbauer KG, Hamburg, Germany

[21] Appl. No.: 522,359

[22] PCT Filed: Mar. 2, 1994

[86] PCT No.: PCT/EP94/00607

§ 371 Date: Nov. 13, 1995

§ 102(e) Date: Nov. 13, 1995

[87] PCT Pub. No.: WO94/20560

PCT Pub. Date: Sep. 15, 1994

[30] Foreign Application Priority Data

Mar. 5, 1993 [DE] Germany ............. 43 07 024.8

[51] Int. Cl.⁶ .................................................. C08G 18/38
[52] U.S. Cl. ........................................... 528/28; 528/29
[58] Field of Search .......................................... 528/28, 29

[56] References Cited

U.S. PATENT DOCUMENTS 4,798,878  1/1989  Brinkmann et al. ..................... 528/28
5,095,045  3/1992  Winkel et al. ........................... 523/115
5,118,290  6/1992  Müller et al. ............................. 433/48

FOREIGN PATENT DOCUMENTS

0170865A1  2/1986  European Pat. Off. ........ C08G 18/10
0410199A2  1/1991  European Pat. Off. ........ C08L 83/08
3636974A1  5/1988  Germany ...................... C08G 18/10

OTHER PUBLICATIONS

International Search Report.

Primary Examiner—Ralph H. Dean
Attorney, Agent, or Firm—Arnold, White & Durkee

[57] ABSTRACT

Plastics with at least one polyaddition product which contains silane, ether, urethane and optionally urea groups and has the following features: a content of terminally located alkoxysilyl groups of the formula $-NR-(CH_2)_m-SiR^1R^2R^3$, in which m is the number 3, R is hydrogen or a group of the formula $-(CH_2)_m-SiR^1R^2R^3$ and at least one of the groups $R^1$, $R^2$ and $R^3$ is a group of the formula $-(O-C_pH_{2p})_q-O-A-R^4$, in which p is the number 3, q is a number in the range from 1 to 100 and A is a single bond and $R^4$ is an organic radical defined in more detail; and the remaining groups $R^1$, $R^2$ and $R^3$ are methyl, ethyl or $C_1$- to $C_4$-alkoxy, the plastics furthermore comprising at least one catalyst for condensation of the silane groups, are suitable as impression, duplicating and modelling compositions, in particular for dental purposes.

12 Claims, No Drawings

PLASTICS WITH A CONTENT OF SILANE, ETHER, URETHANE AND UREA GROUPS AND THEIR USE AS DENTAL COMPOSITION

The invention relates to plastics with at least one polyaddition product which contains silane, ether, urethane and urea groups and has a predominantly linear molecular structure with exclusively aliphatically or cycloaliphatically bonded ether, urethane and urea segments and a number-average molecular weight in the range from 800 to 20,000, the polyaddition product having the following features:

a) a content of polyether groups of 25 to 90, in particular 50 to 80 parts by weight per 100 parts by weight of polyaddition product;

b) a content of urethane groups of the formula I

$$—HN—CO—O— \quad (I)$$

of 0.5 to 10, in particular 1 to 8 parts by weight per 100 parts by weight of polyaddition product;

c) a content of urea groups of the formula II

$$—NH—CO—NH— \quad (II)$$

of 0.5 to 10, in particular 1 to 8 parts by weight per 100 parts by weight of polyaddition product;

d) a content of alkoxysilyl groups, located on both ends of the predominantly linear molecular structure, of the formula III

$$—NR—(CH_2)_m—SiR^1R^2R^3 \quad (III)$$

in which m is the number 3,

R is hydrogen or a group of the formula (IV)

$$—(CH_2)_m—SiR^1R^2R^3 \quad (IV)$$

with the meanings given here for m, $R^1$, $R^2$ and $R^3$, and at least one of the groups $R^1$, $R^2$ and $R^3$ is a group of the formula V

$$—(O—C_pH_{2p})_q—O—A—R^4 \quad (V)$$

in which p is the number 3 and q is a number in the range from 1 to 100, in particular from 2 to 4, and A is a single bond and $R^4$ is an alkyl, aralkyl, vinyl, vinylcarbonyl, alphamethylvinylcarbonyl or beta-methylvinylcarbonyl group, and in which the remaining groups $R^1$, $R^2$ and $R^3$ are methyl, ethyl or $C_1$- to $C_4$-alkoxy, if they are not groups of the above definitions, and the plastics furthermore comprising at least one catalyst for condensation of the silane groups.

Further advantageous embodiments of the invention can be seen from the following description and the subclaims.

The plastics of the invention are particularly suitable as impression and modelling compositions, in particular for dental purposes and for mould construction, which have a low tendency to shrink after complete curing.

Plastics based on polyaddition products containing silane, ether, urethane and urea groups mixed with polymerizable compounds are known from EP-A 0 170 865 and EP-A 0 410 199; the polyaddition products as such are described in DE-A 36 36 974; reference is made to the content of these publications.

The alkoxysilyl groups which occur in the plastics which are already known or in the polyaddition products contained in these have a structure according to the above formula III, in which at least one of the groups $R^1$, $R^2$ and $R^3$ is $C_1$–$C_4$-alkoxy, preferably methoxy or ethoxy, and $R^2$ and $R^3$ can have the same meaning as $R^1$ or are methyl or ethyl groups.

It is preferable if one or two of the groups $R^1$, $R^2$ and $R^3$ in the silyl groups of the formula III are methyl, ethyl or methoxy.

As a result of their content of alkoxysilane groups, these compounds are capable of condensation in the presence of suitable acidic catalysts, elastic, gelatinous polymers being formed as it were as the first stage of curing. Depending on the nature of the polymerizable olefins added, these polymers can then be after-cured to dimensionally stable rigid materials. However, the curing in the first stage specifically leads to unwanted shrinkage processes in impression or modelling compositions, since the condensation products formed during the condensation are incompatible with the polymer material and emerge from the resulting shaped articles, with shrinkage thereof. Thus, products formed during the condensation are incompatible with the polymer material and emerge from the resulting shaped articles, with shrinkage thereof. Thus, for example, in DE-A 36 36 974 a value of 2.2% after 120 minutes is stated for the change in dimensions of the shaped article cured in the first stage for one of the systems mentioned therein; such a material is unusable, in particular, for such dental purposes where extremely high dimensional accuracy is important.

For the plastics known from EP 0 170 865, no data at all have been disclosed on the shrinkage properties during complete curing and on their suitability for dental purposes; furthermore, these plastics have certain disadvantages inasmuch as they are hydrophilic, because of their content of ethyleneoxy groups, and can swell in the presence of water.

The present invention is aimed at plastics of the abovementioned type in which no tendencies to shrink, or considerably reduced tendencies to shrink compared with the prior art, occur after curing and which do not swell on access of water. The invention is based on the finding that the tendencies to shrink can be avoided or reduced if the condensation products liberated in the course of curing are formulated such that they are as compatible as possible with the polyaddition products present as the base structure and therefore do not have the tendency to emerge from the polymer body with shrinkage thereof or to collect on the surface thereof, which means that they are particularly suitable for dental materials. This object is achieved by the abovementioned plastics of the invention.

The polyaddition products on which the plastics of the invention are based can be prepared by reacting aliphatic or cycloaliphatic diisocyanates or mixtures thereof with linear polyethers which have terminal free hydroxyl groups and have a number-average molecular weight in the range from 250 to 6,000, it optionally additionally also being possible to add aliphatic or cycloaliphatic alkanediols or mixtures thereof with a number-average molecular weight in the range from 62 to less than 300. The resulting prepolymers are usually reacted with alkoxysilylmonoamines; aliphatic and/or cycloaliphatic diamines which have primary amino groups and a number-average molecular weight of from 60 to 300 can optionally also be co-used here. The diamines optionally employed serve to establish the particular desired molecular weight.

Diisocyanates which are suitable for this reaction are, in particular, aliphatic or cycloaliphatic diisocyanates in which the diisocyanate groups are bonded to aliphatic hydrocarbon radicals having 2 to 12 carbon atoms or cycloaliphatic or mixed aliphatic-cycloaliphatic hydrocarbon radicals having 4 to 15 carbon atoms.

Typical examples of suitable diisocyanates are ethylene diisocyanate, tetramethylene diisocyanate, hexamethylene diisocyanate, dodecamethylene diisocyanate, cyclobutane 1,3-diisocyanate, cyclohexane 1,3- and 1,4-diisocyanate or 1-isocyanate-3,3,5-trimethyl-5-isocyanatomethyl-cyclohexane or isophorone diisocyanate. Mixtures of the abovementioned diisocyanates can also be employed. Isophorone diisocyanate is particularly preferred.

Polyether-diols which can be employed in the context of the invention can be obtained, in particular, by random polymerization or block polymerization of epoxides, such as ethylene oxide, propylene oxide, butylene oxide, tetrahydrofuran or epichlorohydrin, or else by addition of these epoxides, optionally as a mixture or in succession, onto starting components with reactive hydrogen atoms, such as alcohols or amines, or water, ethylglycol or 1,2-propylene glycol. Those polyethers in which the free OH groups are chiefly primary OH groups are preferably employed.

Diamines which are suitable in the context of the invention are, for example, aliphatic, cycloaliphatic or mixed aliphatic-cycloaliphatic diamines which contain primary amino groups and have a number-average molecular weight in the range from 60 to 300. Typical examples are ethylenediamine, tetramethylenediamine, hexamethylenediamine, 4,4'-diaminodicyclohexylmethane, 1,4-diaminocyclohexane, 1,4-diaminocyclohexane, 4,4'-diamino-3,3'-dimethyldicyclohexylmethane or 1-amino-3,3,5-trimethyl-5-aminomethylcyclohexane (isophoronediamine). 4,4'-Diaminodicyclohexylmethane and isophoronediamine are particularly preferred.

Typical examples of alkanediols are ethylene glycol, 1,2-propylene glycol, 1,4-butylene glycol, 2,3-butylene glycol, 1,6-hexanediol, 1,8-octanediol, neopentylglycol, cyclohexanedimethanol, 1,4-bis-hydroxymethylcyclohexane, 2-methyl-1,3-propanediol, 3-methylpentane-1,5-diol, diethylene glycol, triethylene glycol, tetraethylene glycol, polyethylene glycols, dipropylene glycol, tri- and tetrapropylene glycol, polypropylene glycol, dibutylene glycol and polybutylene glycol.

Suitable alkoxysilylanines for the introduction of alkoxysilyl groups of the general formula III into the plastics of the invention can be prepared, for example, by subjecting the alkoxysilane compounds known for example from DE-A 36 36 974, in particular the commercially obtainable gamma-aminopropyl-tri-$C_1$–$C_4$-alkoxysilanes or bis(3-$C_1$–$C_4$-alkoxysilylpropyl)amines, preferably gamma-aminopropyl-trimethoxy- or -triethoxysilane, to a transesterification with monohydroxy compounds of the general formula VI

$$H-(O-C_pH_{2p})_q-O-A-R^4 \qquad (VI)$$

with the above meanings for p, q, A and $R^4$.

$R^4$ can furthermore contain polymerizable olefinic double bonds; plastics structured in this way then have polycondensation centres, in addition to polymerization centres, and can be cured in two stages. In the first case, high compatibility of the group VI emerging during the condensation with the "backbone" material is to be assumed. In the other case, during subsequent polymerization, for example photopolymerization, redox polymerization or hot polymerization, of the compound (VI) liberated, this is fixed into the "backbone" material. The favourable shrinkage properties of the plastics of the invention follow from this.

If the polyaddition products of the invention do not already contain polymerizable olefinic double bonds, but also if they do, the customary monomers which can be cured by free radicals can be added, in particular monofunctional or polyfunctional (meth)acrylates known per se, in particular methyl methacrylate, isobutyl methacrylate, cyclohexyl methacrylate, ethylene glycol dimethacrylate, diethylene glycol dimethacrylate, polyethylene glycol dimethacrylate, butanediol dimethacrylate, hexanediol dimethacrylate, decanediol dimethacrylate, dodecanediol dimethacrylate, bisphenol A dimethacrylate, trimethylolpropane trimethacrylate and furthermore bis-GMA, as well as reaction products of isocyanates, in particular di- and/or triisocyanates, and methacrylates containing OH groups. Typical examples of the compounds mentioned last are reaction products of 1 mol of hexamethylene diisocyanate with 2 mol of 2-hydroxyethyl methacrylate, of 1 mol of tris(6-isocyanatohexyl) isocyanurate with 3 mol of hydroxyethyl methacrylate, and of 1 mol of trimethylhexamethylene diisocyanate with 2 mol of hydroxyethyl methacrylate. The content of these compounds in the mixture with the silicopolyether or silicopolyethers can vary between 5 and 90% by weight. Dye-stuffs, optionally also those which result in a change in colour when complete curing has taken place, can furthermore also be added to the plastics of the invention, and, in addition, also emulsifiers for establishing the rheological properties, antibiotics, haemostatic agents and the like. The filler content in the plastic of the invention can in general be in the range from 40 to 80% by weight.

The invention is explained in more detail in the following with the aid of preferred embodiment examples and comparison examples.

Comparison Example 1 a) 912.5 g (0.5 mol of OH) of a linear polyether-diol (molecular weight 3,650, block copolymer prepared by polyaddition of 80 parts by weight of propylene oxide onto propylene glycol and subsequent polyaddition of 30 parts by weight of ethylene oxide) were dried at 100° C. under an oil pump vacuum (0.2 hPa) for 1 hour. After the mixture had cooled to room temperature, 111 g (0.5 mol) of isophorone diisocyanate and 1 drop of tin ethylhexanoate were added to the mixture. The mixture was heated to 100° C. under a gentle stream of nitrogen and left at this temperature for 60 minutes. After cooling to room temperature, the NCO index of the prepolymer was determined:

NCO found: 1.87%

NCO calculated: 2.05%

89.65 g (0.5 mol) of 3-aminopropyltrimethoxysilane were then added dropwise in the course of 2 hours, so that only moderate heating of the reaction mixture occurred. After the mixture had been stirred at room temperature for a further hour, an NCO band could no longer be detected in the IR spectrum.

The poly(ether-urethane-urea) formed is a clear, only slightly yellowish-coloured composition with good flow properties.

b) To crosslink the prepolymers prepared in the above Stage a), a hardener substance comprising 15% by weight of phosphoric acid, 35% by weight of water (doubly distilled) and 50% by weight of glycerol is stirred together.

20 g of prepolymer from Stage a) are stirred with 0.7 g of the abovementioned hardener liquid on a mixing block for 30 seconds.

The composition cures completely within a few minutes to give an elastic, non-tacky shaped article.

The change in dimensions, determined in accordance with ISO 4823 (dry storage, 23° C.), is: 30 minutes 0.1%

60 minutes 0.2%

120 minutes 0.3 %

12 hours 1.0%

24 hours 1.1

EXAMPLE 1 a) The procedure is as described in Comparison Example 1, Stage a), except that 221.8 g (0.5 mol) of 3-aminopropyl-tris(2-methoxyethoxyethoxy) silane are added dropwise as the aminosilane compound. The resulting poly(ether-urethane-urea) likewise has good flow properties and is clear and slightly yellowish-coloured.

b) 20 g of prepolymer from Stage b) are stirred with 0.6 g of the hardener liquid described under Comparison Example 1, Stage b) on a mixing block for 30 seconds. The composition cures completely within a few minutes to give a rubbery-elastic, non-tacky body.

The change in dimensions (dry storage, 23° C., ISO 4823) is:

30 minutes 0%

60 minutes 0%

120 minutes 0%

12 hours 0.5%

24 hours 1.1%

EXAMPLE 2 a) 89.65 g (0.5 mol) of 3-aminopropyltrimethoxysilane and 525 g (1.5 mol) of polyethylene glycol monomethyl ether (molecular weight 350) are initially stirred with 0.1 g of sodium at 80° C. for 3 hours until the sodium has dissolved. The mixture is then heated to 150° C. and the methanol formed from the transesterification reaction is distilled off and collected. After 12 hours, the mixture is cooled to 70° C. and an oil pump vacuum (2 hPa) is applied for 5 hours. The mixture is then cooled in a stream of nitrogen.

b) 582.65 g of the transesterification product obtained above in Stage a) are added dropwise to the prepolymer obtained in Comparison Example 1 of Stage a) from 912.5 g of linear polyether-diol and 111 g of isophorone diisocyanate. Isocyanate groups can then no longer be detected by infrared spectroscopy.

c) A hardener paste comprising 33% by weight of phosphoric acid, 17% by weight of water (doubly distilled) and 50% by weight of glycerol is then mixed.

20 g of the substance from Stage b) and 0.93 g of the hardener paste are mixed on a mixing block for 30 seconds. The composition cures completely within a few minutes to give a rubbery-elastic, non-tacky solid.

The physical properties were determined in accordance with ISO 4823. The change in dimensions is:

after 30 minutes: 0.0% after 60 minutes: 0.0% after 2 hours: 0.0% after 5 hours: 0.17% after 24 hours: 0.8%

EXAMPLE 3 a) 44.82 g (0.25 mol) of 3-aminopropyltrimethoxysilane and 525 g (0.75 mol) of polypropylene glycol monobutyl ether (molecular weight=700) are initially stirred with 0.1 g of sodium at 80° C. for 3 hours until the sodium has dissolved. The mixture is then heated to 150° C. and the methanol formed from the transesterification reaction is distilled off and collected. After 12 hours, the mixture is cooled to 70° C. and an oil pump vacuum (2 mbar) is applied for 5 hours. The mixture is then cooled in a stream of nitrogen.

b) The procedure is as described in Comparison Example 1. However, 500 g (0.25 mol of OH) of polypropylene glycol (molecular weight 4000), as the linear polyetherdiol, and correspondingly 55.57 g (0.25 mol) of isophorone diisocyanate are employed. 553.75 g of the transesterification product from Stage a) are added dropwise as the aminosilane reaction partner in the course of 2 hours. Isocyanate groups can then no longer be detected by infrared spectroscopy.

c) A hardener paste comprising 42.5% by weight of phosphoric acid, 7.5% by weight of water (double-distilled) and 50% by weight of glycerol is mixed.

20 g of the substance from Stage b) and 1.63 g of the hardener paste are mixed on a mixing block for 30 seconds. The composition cures completely within a few minutes to give a rubbery-elastic, non-tacky solid.

The change in dimensions, determined in accordance with ISO 4823, dry storage, 23° C., is:

| | |
|---|---|
| after 30 minutes: | 0.0 % |
| after 60 minutes: | 0.0 % |
| after 2 hours: | 0.2 % |
| after 5 hours: | 0.2 % |
| after 24 hours: | 0.4%. |

EXAMPLE 4 a) Transesterification 17.93 g (0.1 mol) of 3-aminopropyltrimethoxysilane and 123.77 g. (0.6 mol) of tripropylene glycol monomethyl ether are initially stirred with 0.1 g of sodium at 60° C. with exclusion of moisture for 2 hours. After the sodium has dissolved, the temperature is increased to 150° C. in the course of 4 hours and the methanol formed during the transesterification reaction is distilled off and collected. After 12 hours, an oil pump vacuum is applied at this temperature for 5 hours. 55.76 g (0.27 mol) of excess tripropylene glycol monomethyl ether thereby distill off.

n=1.4295 (literature: 1.4300)

Determination of the amine content of the transesterification product remaining in the distillation sump shows that quantitative replacement of the methoxy groups has taken place.

Amine content: calculated: 2.26% found: 2.28% (3-aminopropyl-tris (2-methoxytripropoxy)silane b) Preparation of the prepolymer The procedure is as described in Comparison Example 1. However, 40 g (8 mmol) of polypropylene glycol (molecular weight 4000), as the linear polyether-diol, and correspondingly 3.56 g (16 mmol) of isophorone diisocyanate are employed. 11.23 g (16 mmol) of the transesterification product from Example 9 are added dropwise as the aminosilane reaction partner. After the mixture has been stirred at room temperature for 4 hours, isocyanate can no longer be detected by infrared spectroscopy.

We claim:

1. A plastic for use in making an impression, duplicate or model and having a low tendency to shrink after complete curing, the plastic having at least one predominantly linear polyaddition product comprising silane and aliphatically or cycloaliphatically bound ether, urethane and urea groups and a number average molecular weight of from 800 to 20,000, wherein the polyaddition product has:

a) ether groups contained in a polyether and constituting 25 to 90 parts by weight per 100 parts by weight of polyaddition product;

b) urethane groups of the formula $$-\text{HN}-\text{CO}-\text{O}-$$

at a content of 0.5 to 10 parts by weight per 100 parts by weight of polyaddition product;

c) urea groups of the formula $$-\text{NH}-\text{CO}-\text{NH}-$$

at a content of 0.5 to 10 parts by weight per 100 parts by weight of polyaddition product;

d) silanes that are alkoxysilyl groups located on both ends of the predominantly linear polyaddition product and have the formula $$-\text{NR}-(\text{CH}_2)_m-\text{SiR}^1\text{R}^2\text{R}^3$$

in which m is 3,

R is hydrogen or a group of the formula:

$$-(\text{CH}_2)_m-\text{SiR}^1\text{R}^2\text{R}^3$$

where $R^1$, $R^2$ and $R^3$ are methyl, ethyl, $C_1$ to $C_4$ alkoxy or $-(O-C_pH_{2p})_q-O-A-R^4$, and at least one of $R^1$, $R^2$ and $R^3$ is $$-(O-C_pH_{2p})-O-A-R^4$$

in which p is 3;

q is from 1 to 100;

A is a single bond and $R^4$ is alkyl, aralkyl, vinyl, vinylcarbonyl, alpha-methylvinylcarbonyl or beta-methylvinylcarbonyl.

2. The plastic according to claim 1, where at least one of $R^1$, $R^2$ and $R^3$ in $NR-(CH_2)_m-SiR^1R^2R^3$ is methyl, ethyl or methoxy.

3. The plastic according to claim 1 or 2 defined further as comprising at least one mono- or polyfunctional (meth)acrylate curable by means of free radicals and at least one catalyst for hot polymerization, cold polymerization or photopolymerization of the (meth)acrylate.

4. The plastic of claim 1 where the polyether constitutes 50 to 80 parts by weight per 100 parts by weight of polyaddition product.

5. The plastic of claim 1 where the urethane groups constitute 1 to 8 parts by weight per 100 parts by weight of polyaddition product.

6. The plastic of claim 1 where the urea groups constitute 1 to 8 parts by weight per 100 parts by weight of polyaddition product.

7. The plastic of claim 1 where q is from 2 to 4.

8. The plastic of claim 1 defined further as comprising a catalyst for silane condensation.

9. An impression, duplicate or model comprising the plastic of claim 1.

10. A method of preparing an impression, duplicate or model, the method comprising preparing a plastic with a low tendency to shrink after complete curing, the plastic having at least one polyaddition product which contains alkoxysilyl and aliphatically or cycloaliphatically bonded polyether and urethane groups and has a predominantly linear molecular structure and a number average molecular weight of from 800 to 20,000, the polyaddition product having:

a) ether groups contained in a polyether and constituting 25 to 90 parts by weight per 100 parts by weight of polyaddition product;

b) urethane groups of the formula $$-\text{HN}-\text{CO}-\text{O}-$$

at a content of 0.5 to 10 parts by weight parts 100 parts by weight of polyaddition product;

c) urea groups of the formula $$-\text{NH}-\text{CO}-\text{NH}-$$

at a content of 0.5 to 10 parts by weight per 100 parts by weight of polyaddition product;

d) silanes that are alkoxysilyl groups located on both ends of the predominantly linear polyaddition product and have the formula $$-\text{NR}-(\text{CH}_2)_m-\text{SiR}^1\text{R}^2\text{R}^3$$

in which m is 3,

R is hydrogen or a group of the formula:

$$-(\text{CH}_2)_m-\text{SiR}^1\text{R}^2\text{R}^3$$

where $R^1$, $R^2$ and $R^3$ are methyl, ethyl, $C_1$ to $C_4$ alkoxy or $-(O-C_pH_{2p})_q-O-A-R^4$, and at least one of $R^1$, $R^2$ and $R^3$ is $$-(O-C_pH_{2p})-O-A-R^4$$

in which p is from 2 to 4;

q is from 1 to 100;

A is a single bond and $R^4$ is alkyl, aralkyl, vinyl, vinylcarbonyl, alpha-methylvinylcarbonyl or beta-methylvinylcarbonyl;

and preparing an impression, duplicate or model from the plastic.

11. The method according to claim 10, characterized in that at least one of $R^1$, $R^2$ and $R^3$ of $-NR-(CH_2)_m-SiR^1R^2R^3$ is methyl, ethyl or methoxy.

12. The method acording to claim 10 or 11 wherein the plastic comprises at least one mono- or polyfunctional (meth)acrylate curable by means of free radicals and at least one catalyst for hot polymerization, cold ppolymerization or photopolymerization, as polymer compositions which cure in several stages.

* * * * *

UNITED STATES PATENT AND TRADEMARK OFFICE
CERTIFICATE OF CORRECTION

PATENT NO. : 5,739,245

DATED : April 14, 1998

INVENTOR(S) : Lubbers et al.

It is certified that error appears in the above-identified patent and that said Letters Patent is hereby corrected as shown below:

In claim 1, column 7, line 32, after ')' insert --q--.
In claim 10, column 8, line 40, after ')' insert --q--.
In claim 12, column 8, line 37, delete "ppolymerization" and insert --polymerization--.

Signed and Sealed this

Thirtieth Day of June, 1998

Attest:

BRUCE LEHMAN

Attesting Officer

Commissioner of Patents and Trademarks